US004001749B2

United States Statutory Invention Registration [19]

[11] Reg. Number: H1749

Colle et al.

[45] Published: Sep. 1, 1998

[54] METHOD FOR INHIBITING HYDRATE FORMATION

[75] Inventors: Karla Schall Colle, Houston, Tex.; Christine Ann Costello, Easton, Pa.; Russell Harlan Oelfke, Houston, Tex.; Dennis George Peiffer, Annandale; Manese Rabeony, Piscataway, both of N.J.; Larry D. Talley, Friendswood, Tex.; Pamela Jean Wright, Easton, Pa.

[73] Assignee: Exxon Production Research Company, Houston, Tex.

[21] Appl. No.: 306,568

[22] Filed: Sep. 15, 1994

[51] Int. Cl.[6] ..... C07C 9/00

[52] U.S. Cl. ..... 585/15

[58] Field of Search ..... 585/15, 950; 166/310, 166/371; 137/3, 13

[56] References Cited

U.S. PATENT DOCUMENTS

| | | | |
|---|---|---|---|
| 3,741,961 | 6/1973 | Kmiecik et al. | 260/243 R |
| 4,203,900 | 5/1980 | Kaiser | 548/239 |
| 4,354,029 | 10/1982 | Kaiser et al. | 548/239 |
| 4,856,593 | 8/1989 | Matthews et al. | 106/310 |
| 4,915,176 | 4/1990 | Sugier et al. | 166/371 |
| 4,973,775 | 11/1990 | Sugier et al. | 585/15 |
| 5,076,364 | 12/1991 | Hale et al. | 166/310 |
| 5,076,373 | 12/1991 | Hale et al. | 175/40 |
| 5,244,878 | 9/1993 | Sugier et al. | 507/90 |
| 5,331,105 | 7/1994 | Duncum et al. | 585/800 |

FOREIGN PATENT DOCUMENTS

| | | |
|---|---|---|
| 0104042 A2 | 3/1984 | European Pat. Off. . |
| 0309210 A1 | 3/1989 | European Pat. Off. . |
| 0336501 A2 | 10/1989 | European Pat. Off. . |
| 0457375 A1 | 11/1991 | European Pat. Off. . |
| 0536950 A1 | 4/1993 | European Pat. Off. . |
| 0582507 A1 | 2/1994 | European Pat. Off. . |
| 0594479 A1 | 4/1994 | European Pat. Off. . |
| 2618876 | 2/1989 | France . |
| 1391692 | 4/1988 | U.S.S.R. . |
| 1683807 A1 | 10/1991 | U.S.S.R. . |
| 1799286 A3 | 2/1993 | U.S.S.R. . |
| PCT/EP3/01519 | 12/1993 | WIPO . |
| PCT/US93/11191 | 6/1994 | WIPO . |

OTHER PUBLICATIONS

U.S. application No. 07/979,588 by E. D. Sloan, Jr., filed Nov. 20, 1992.

U.S. application No. 08/083,103 by E. D. Sloan, Jr., filed Jun. 24, 1993.

"Recent Syntheses and Reactions of Cyclic Imidic Esters," Seeliger et al., *Angew. Chem. Int. Ed.*, vol. 5, No. 10, 875–88 (1966).

"Block Copolymers from Cyclic Imino Ethers: A New Class of Nonionic Polymer Surfactant," Kobayashi et al., *Macromolecules*, vol. 19, p. 535, (1986).

*Polymer Syntheses*, S. R. Sandler and W. Karo, vol. 1 (2nd Ed.), Chapter 12, Academic Press: New York, 1992.

"Copolymerization of Vinylene Carbonate," Hayashi, K. and Smets, G., *J. Polym. Sci.*, vol. 27, p. 275 (1958).

"Effect of Surfactants on Hydrate Formation Kinetics," Kalogerakis et al. SPE 1993 International Oilfield Chemistry Symposium (new Orleans, Mar. 2–5, 1993) Proceedings 375–83 (1993).

"Surfactants in Oil Production," Muijs, R. Soc. Chem., (Chemical Oil Ind. Developments & Applications) V 97, 277–97, 1991.

"A Molecular Mechanism for Gas Hydrate Nucleation from Ice," Sloan, et al. AIChE Journal, vol. 37, No. 9, 1281–92, (Sep. 1991).

"Surfactants Studies as Hydrate–Formation Inhibitors," Kuliev et al., Gazovoe Delo (1972), (10), 17–19. (Translation enclosed).

"Effect of Lower Alcohols on Formation of Crystallohydrates of Liquids and Gases," Krasnov, Gazovoe Delo (1966), (12), 9–11 (Translation enclosed).

"Clathrate Hydrates," P. Englezos, Ind. Eng. Chem. Res. 1993, 32, 1251–1274.

"Recent Developments in Gas Dehydration and Hydrate Inhibition," Hubbard et al., SPE 21507, pp. 263–276 (1991).

"Natural Gas Hydrate Phase Equilibria and Kinetics: Understanding the State of the Art," Sloan, Revue De L'Institut Francais Du Petrole, (continued) vol. 45, No. 2, Mars–Avril 1990. Presented Jun. 8, 1989.

*Primary Examiner*—Charles T. Jordan
*Assistant Examiner*—Meena Chelliah
*Attorney, Agent, or Firm*—Kurt D. Van Tassel

[57] ABSTRACT

A method for inhibiting the formation of clathrate hydrates in a fluid having hydrate forming constituents is disclosed. More specifically, the method can be used in treating a petroleum fluid stream such as natural gas conveyed in a pipe to inhibit the formation of a hydrate restriction in the pipe. The method uses a mixture comprising a first additive and a second additive. The mixture produces a synergistic hydrate inhibition effect. The first additive is selected from the class of substantially water soluble polymers. The second additive is selected from the class of ionic or non-ionic organic compounds which have a polar part and nonpolar part with the nonpolar part having an alkyl, alkenyl, or alkynyl group with 12 or fewer carbon atoms.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR INHIBITING HYDRATE FORMATION

Related to copending U.S. patent applications, Ser. Nos. 08/306,331 and 08/306,336, each filed in the name of K. S. Colle, et al. on Sep. 15, 1994, Ser. No. 08/306,331 patented on Feb. 13, 1996, U.S. Pat. No. 5,491,269 and Ser. No. 08/306,336 abandoned on Sep. 28, 1995.

FIELD OF THE INVENTION

The present invention relates to a method for inhibiting the formation of clathrate hydrates in a fluid. More specifically, the invention relates to a method for inhibiting the formation of gas hydrates in a pipe used to convey oil or gas.

BACKGROUND OF THE INVENTION

Carbon dioxide, hydrogen sulfide, and various hydrocarbons, such as methane, ethane, propane, normal butane and isobutane, are present in natural gas and other petroleum fluids. However, water is typically found mixed in varying amounts with such petroleum fluid constituents. Under conditions of elevated pressure and reduced temperature clathrate hydrates can form when such petroleum fluid constituents or other hydrate formers are mixed with water. Clathrate hydrates are water crystals which form a cage-like structure around guest molecules such as hydrate forming hydrocarbons or gases. Some hydrate forming hydrocarbons include, but are not limited to, methane, ethane, propane, isobutane, butane, neopentane, ethylene, propylene, isobutylene, cyclopropane, cyclobutane, cyclopentane, cyclohexane, and benzene. Some hydrate forming gases include, but are not limited to, oxygen, nitrogen, hydrogen sulfide, carbon dioxide, sulfur dioxide, and chlorine.

Gas hydrate crystals or gas hydrates are a class of clathrate hydrates of particular interest to the petroleum industry because of the pipeline blockages that they can produce during the production and/or transport of the natural gas and other petroleum fluids. For example, at a pressure of about 1 MPa ethane can form gas hydrates at temperatures below 4° C., and at a pressure of 3MPa ethane can form gas hydrates at temperatures below 14° C. Such temperatures and pressures are not uncommon for many operating environments where natural gas and other petroleum fluids are produced and transported.

As gas hydrates agglomerate they can produce hydrate blockages in the pipe or conduit used to produce and/or transport natural gas or other petroleum fluid. The formation of such hydrate blockages can lead to a shutdown in production and thus substantial financial losses. Furthermore, restarting a shutdown facility, particularly an offshore production or transport facility, can be difficult because significant amounts of time, energy, and materials, as well as various engineering adjustments, are often required to safely remove the hydrate blockage.

A variety of measures have been used by the oil and gas industry to prevent the formation of hydrate blockages in oil or gas streams. Such measures include maintaining the temperature and/or pressure outside hydrate formation conditions and introducing an antifreeze such as methanol, ethanol, propanol, or ethylene glycol. From an engineering standpoint, maintaining temperature and/or pressure outside hydrate formation conditions requires design and equipment modifications, such as insulated or jacketed piping. Such modifications are costly to implement and maintain. The amount of antifreeze required to prevent hydrate blockages is typically between 10% to 20% by weight of the water present in the oil or gas stream. Consequently, several thousand gallons per day of such solvents can be required. Such quantities present handling, storage, recovery, and potential toxicity issues to deal with. Moreover, these solvents are difficult to completely recover from the production or transportation stream.

Consequently, there is a need for a combination of gas hydrate additives that can be conveniently mixed at low concentrations in the produced or transported petroleum fluids. Such an additive mixture should reduce the rate of nucleation, growth, and/or agglomeration of gas hydrate crystals in a petroleum fluid stream and thereby inhibit the formation of a hydrate blockage in the pipe conveying the petroleum fluid stream.

One method of practicing the present invention uses a first gas hydrate additive in combination with a second gas hydrate additive in the concentration ranges of about 0.01% to about 5% and about 0.05% to about 6%, respectively, by weight of the water present in the oil or gas stream. As discussed more fully below, the additives of this invention can effectively treat a petroleum fluid having a water phase.

SUMMARY OF THE INVENTION

According to the invention there is provided a method for inhibiting the formation of clathrate hydrates in a fluid having water and other hydrate forming constituents. The method comprises treating the fluid with a first additive and a second additive, the first additive comprising a substantially water soluble polymer and having a first independent effect on the formation of clathrate hydrates in the fluid, the second additive comprising a substantially polar part and a substantially nonpolar part, wherein the nonpolar part is an alkyl, alkenyl, or alkynyl group with 12 or fewer carbon atoms and having a second independent effect on the formation of clathrate hydrates in the fluid, thereby producing a total inhibition effect for the fluid which is greater than the combination of the first and second independent effects for the fluid.

The invention can be practiced using any one of various treatment methods including, but not limited to, (1) treating the fluid with the first and second additive substantially simultaneously, (2) treating the fluid first with the first additive and treating it second with the second additive, or (3) treating the fluid first with the second additive and treating it second with the first additive.

The first additive comprises a water soluble polymer including, but not limited to, those selected from the group consisting of polyvinyllactams, polyalkylacrylamides, and polyalkyloxazolines, polyvinylcarboxylates, and copolymers thereof. The second additive comprises those organic compounds selected from the group consisting of anionic, cationic, non-ionic, zwitterionic organic compounds and mixtures thereof. Such second additives include, but are not limited to, those selected from the group consisting of alcohols, ethers, and organic salts.

DETAILED DESCRIPTION OF THE INVENTION

INVENTIVE METHOD

The claimed method inhibits the formation of clathrate hydrates in a fluid having hydrate forming constituents. Formation of clathrate hydrates means the nucleation, growth, and/or agglomeration of clathrate hydrates. Such clathrate hydrates may be formed in a fluid whether it is flowing or substantially stationary, but are often most problematic in flowing fluid streams conveyed in a pipe. For example, flow restrictions arising from partial or complete blockages in a fluid stream can arise as clathrate hydrates adhere to and accumulate along the inside wall of the pipe used to convey the fluid. Nonetheless, the invention can be used for inhibiting formation of clathrate hydrates in substantially stationary fluids.

Without limiting the scope of the invention, applicants' believe that the combination of additives used in practicing the invention inhibit the nucleation but primarily inhibit the growth and/or agglomeration of clathrate hydrates. Therefore, clathrate hydrates can be produced in the practice of the invention. Such hydrates, however, will have a substantially reduced tendency to grow and/or agglomerate.

In one embodiment of the invention, a concentrated solution or mixture of a first additive comprising one or more substantially water soluble polymeric additives, and a second additive comprising one or more anionic, cationic, non-ionic, or zwitterionic organic compounds is introduced into a petroleum fluid stream having an aqueous phase. As the solution or mixture of additives described in this invention is substantially dissolved in the aqueous phase or dispersed in the fluid stream it reduces the rate that clathrate hydrates are formed and reduces their tendency to agglomerate into large masses, thereby reducing the tendency for a flow restriction to occur.

In a preferred embodiment, the first and second additive are first dissolved into an appropriate carrier solvent or liquid to make a concentrated solution or mixture. It should be understood that many liquids may effectively facilitate treatment of the fluid stream without dissolving the additives. Because many of such liquids will preferably dissolve the additives, for convenience, they are referred to hereafter as solvents whether they produce an additive solution, emulsion, or other type of mixture. The solvent's principal purpose is to act as a carrier for the first and second additive and to facilitate their absorption into the aqueous phase of the petroleum fluid. Any solvent suitable for delivering the additives to the fluid's aqueous phase may be used. Such solvents include, but are not limited to, water, brine, sea water, produced water, methanol, ethanol, propanol, isopropanol, glycol or mixtures of such solvents. Other solvents familiar to those skilled in the art may also be used.

It should be understood that the use of a carrier solvent is not required in the practice of the invention, but it is a convenient method of introducing the additive into the fluid. In many applications the use of a carrier solvent will facilitate treatment of the fluid stream. It should also be understood that the two additives do not need to be mixed in the same carrier solvent. They can be mixed individually, in separate solvents, and introduced separately into the petroleum fluid. Alternatively, some of the second additives listed below do not need carrier solvents because they are liquids at normal ambient temperatures and pressures.

Any convenient concentration of the additive in the carrier solvent can be used, so long as it results in the desired final concentration in the aqueous phase of the petroleum fluid. Higher concentrations are preferred, since they result in a reduced volume of concentrated mixture to handle and inject into the petroleum stream. The actual concentration used in a specific application will vary depending upon the selection of carrier solvent, the chemical composition of the first and second additive, the system temperature, and the solubility of the additives in the carrier solvent at application conditions. In the preferred embodiment, the concentration of the organic compound additive is about four times that of the polymeric additive.

The additive mixture is introduced into the aqueous phase of the petroleum fluid using mechanical equipment, such as, chemical injection pumps, piping tees, injection fittings, and other devices which will be apparent to those skilled in the art. However, such equipment is not essential to practicing the invention. To ensure an efficient and effective treatment of the petroleum fluid with the additive mixture three points should be carefully considered.

First, an aqueous phase is preferably present at the location the additive mixture is introduced into the fluid. In some petroleum fluid systems (particularly natural gas systems), an aqueous phase does not appear until the gas has cooled sufficiently for water to condense. If this is the case, the additive mixture is preferably introduced after the water has condensed. Alternatively, in the event that an aqueous phase is not available at the point the additive mixture is introduced, the additive mixture concentration should be selected to ensure that the additive mixture's viscosity is sufficiently low to facilitate its dispersion through the fluid and permit it to reach the aqueous phase.

Second, because the additives primarily serve to inhibit the formation of clathrate hydrates, rather than reverse such formation, it is important to treat the fluid prior to substantial formation of clathrate hydrates. As a wet petroleum fluid cools it will eventually reach a temperature, known as the hydrate equilibrium dissociation temperature or $T_{eq}$, below which hydrate formation is thermodynamically favored. A petroleum fluid's $T_{eq}$ will shift as the pressure applied to the fluid and its composition change. Various methods of determining a fluid's $T_{eq}$ at various fluid compositions and pressure are well known to those skilled in the art. Preferably, the fluid should be treated with the first and second additives when the fluid is at a temperature greater than $T_{eq}$. It is possible, but not preferable, to introduce the additives while the temperature is at or slightly below $T_{eq}$, preferably before clathrate hydrates have begun to form.

Third, in the practice of the invention, hydrate nucleation and growth is inhibited but nonetheless hydrates can form, while the tendency for them to agglomerate is substantially reduced. Therefore, dispersed hydrates may be present in a petroleum fluid stream. Preferably, before further processing of the petroleum fluid stream occurs, the fluid stream is gradually warmed to a temperature above its $T_{eq}$ to ensure any solid hydrates are melted and do not interfere with other processes.

The quantity of the first additive introduced into a petroleum fluid with an aqueous phase solvent will typically vary between about 0.01 wt % to about 5 wt % by weight of the water present in the fluid. The quantity of the second additive introduced into a petroleum fluid with an aqueous phase solvent will typically vary between about 0.05% to about 6% by weight of the water present in the fluid. Preferably, the first additive concentration will be about 0.5 wt % and the second additive will be about 2 wt %. For example, a laboratory study has shown that 0.5 wt % poly(2-ethyl-2-oxazoline) with 2 wt % sodium butyl sulfate allowed a petroleum fluid to cool to a temperature which was about 17° C. below its $T_{eq}$ without formation of a hydrate blockage. At this temperature level, hydrate nucleation occurred, but hydrate growth was significantly retarded, hydrate agglomeration was not seen, and no hydrate blockage occurred. A higher concentration of the additives can be used to lower the temperature at which a hydrate blockage is obtained. A suitable concentration for a particular application, however, can be determined by those skilled in the art by taking into account the additive's performance under such application, the degree of inhibition required for the petroleum fluid, and the additive's cost.

ADDITIVE SYNTHESIS

Several polymeric and ionic and non-ionic organic additives were either synthesized or obtained commercially for evaluating either alone or in combination with each other in the tetrahydrofuran (THF) test described below. The chemical structures and names for the polymeric additives which were evaluated are:

PDMAM = Poly(N,N-dimethylacrylamide)

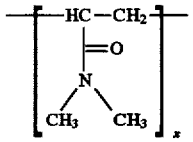

PDEAM = Poly(N,N-diethylacrylamide)

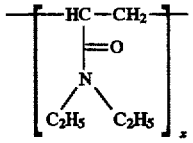

PMAM = Poly(N-methylacrylamide)

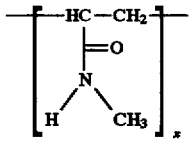

PEOx = Poly(2-ethyl-2-oxazoline)

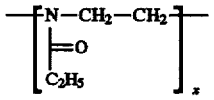

PVP = Poly(vinylpyrrolidone)

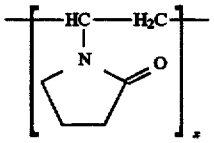

PVCap = Poly(vinylcaprolactam)

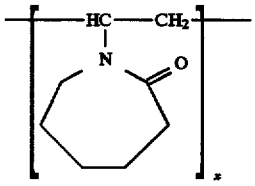

-continued

VP/VPro = Copolymer of N-vinyl pyrrolidone and vinyl propionate

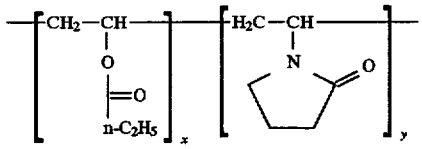

VP/SPP = Copolymer of N-vinyl pyrrolidone and N-(3-sulfopropyl)-N-methacryloylamidopropyl-N,N-dimethylammonium betaine

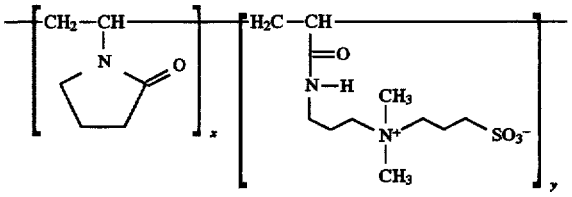

PEFAm = Poly(ethenylformamide)

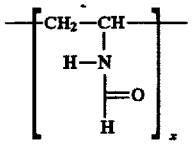

where x and y are average integers sufficient to produce an average molecular weight between about 1,000 and about 1,000,000.

Regarding a polymer's average molecular weight, it is well understood by those skilled in the art that a given polymer composition is comprised of polymers having variable chain lengths and molecular weights, with some above and some below the polymer's average molecular weight. Therefore, some polymer chains contain less than x repeating units and some polymer chains contain more than x repeating units. Accordingly, x represents an average number of repeating units over the distribution of polymer chains comprising a given polymer composition.

The chemical names and structures of the various organic additives evaluated either alone or in combination with the polymeric additives identified above are provided below.

| | |
|---|---|
| Na C4 Sulfate = Sodium salt of n-butyl sulfate | $H_3C-H_2C-H_2C-CH_2-O-SO_3^-Na^+$ |
| Na C4 Sulfonate = Sodium salt of n-butyl sulfonic acid | $H_3C-H_2C-H_2C-CH_2-SO_3^-Na^+$ |
| Na C8 Sulfonate = Sodium salt of n-octyl sulfonic acid | $H_3C-(H_2C)_7-SO3^-Na^+$ |
| Na Valerate = Sodium salt of valeric acid (n-pentanoic acid) | 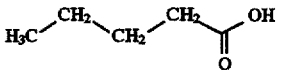 |
| Butyl Zwitterion = C4 Zwitterion | $CH_3-(CH_2)_3-{}^+N-(CH_3)_2-(CH_2)_4-SO_3^-$ |
| MeOH = Methanol | $H_3C-OH$ |

Most of the polymers tested are commercially available. Several of the polymers tested, VP/VPro, VP/SPP, and polyalkylacrylamides, are polymers synthesized according to known literature procedures. VP/VPro is prepared by copolymerizing vinyllpyrrolidone and vinyl propionate, both commercially available monomers, using known procedures (Hayashi and Smets, *J. Polym. Sci.*, 27, 275 (1958) or EP 0 104 042 A2). VP/SPP is prepared as described by Schulz, et al. in "Polymers In Aqueous Media—Performance Through Association," *Advances in Chemistry Series*, 223, American Chemical Society, Washington, D.C., 1989, Chapter 9. The ionic and non-ionic organic additives are all commercially available materials or can be produced by neutralization of commercially available precursors.

ADDITIVE EVALUATION

Laboratory Evaluation Procedure

One method for evaluating an additive's effectiveness is a bench-scale atmospheric pressure test often referred to as a tetrahydrofuran or THF test. A THF test typically uses 3mL of tetrahydrofuran (THF) and 9 mL of ASTM synthetic seawater (SSW) containing the desired amount of additive. The THF and SSW are placed in a capped test tube (15 mm OD×12.5 cm long) with a 0.95 centimeter stainless steel ball. Each tube is placed in a ferriswheel-type holder and placed in a cooling bath held near 0° C. The tubes are rotated to facilitate mixing of the samples. The tubes are monitored visually and recorded with a video camera. As hydrate formation proceeds the viscosity of THF/SSW solution increases. In many instances the solution's viscosity will become high enough for the ball to stop moving. The time required for the stainless steel ball to stop moving the full length of the tube is referred to as ball stop time or BST.

The BST is an approximate indication of an additive's effectiveness. Because the THF/SSW solution has a $T_{eq}$ of about 2°–5° C. and THF is miscible with water, hydrate formation is substantially accelerated for the THF/SSW solution as compared to petroleum fluids conveyed in a pipeline or flowline under typical field conditions. Therefore, BSTs are useful for indicating which additives may be effective under field applications. A BST for a THF/SSW solution with an additive which is about three times the BST for a THF/SSW control solution with no additive present indicates that the additive demonstrates a threshold inhibition effect. Therefore, as used herein, a threshold inhibition concentration ("TIC") means the additive concentration in a THF/SSW solution required to produce a BST which is about three times the BST for a THF/SSW control solution.

Some additives may have a BST indicating a nominal or no inhibition effect compared to the BST for the THF/SSW control solution ("control BST") or a BST indicating formation of hydrates is accelerated compared to the control BST. Consequently, an additive with a BST which is equal to the control BST is identified as having no inhibition effect or a null effect. An additive with a BST which is between the control BST and about three times the control BST is identified as having a nominal inhibition effect. An additive with a BST which is less than the control BST is identified as having an a hydrate activation effect. A hydrate activation effect indicates that an additive with such a BST accelerates or enhances the rate of hydrate formation compared to the THF/SSW control.

Because the THF test results are sensitive to variations in the temperature at which the test is run, rotation frequency of the tube, clearances between the stainless steel ball and tube wall, etc., it is important to run a THF/SSW control solution with each additive evaluation to ensure that an additive's TIC is accurately measured and that a reliable threshold inhibition effect is observed.

THF Test Results

Without limiting the scope of the invention, and for the purpose of illustrating the invention, various polymeric and organic additives were evaluated alone and in combination with each other including PVP, PEOx, PVCap, VP/VPro, VP/SPP, PEFAm, PDMAM, PDEAM, PMAM, Na C4 Sulfate, Na C4 Sulfonate, Na C8 Sulfonate, Na Valerate, C4 Zwitterion and MeOH.

TABLE 1

THF TEST RESULTS

| FIRST ADDITIVE | CONC., WT % | SECOND ADDITIVE | CONC., WT % | BALLSTOP TIME (MIN) |
|---|---|---|---|---|
| None | — | None | — | 7 |
| None | — | Na C4 Sulfate | 2.0 | 15 |
| None | — | Na C4 Sulfonate | 2.0 | 27 |
| None | — | Na C8 Sulfonate | 2.0 | 20 |
| None | — | Na Valerate | 1.0 | 10 |
| None | — | C4 Zwitterion | 2.0 | <20 |
| None | — | MeOH | 1.0 | 31 |
| PVP | 0.4 | None | — | 177 |
| PEOx | 0.5 | None | — | 87 |
| PVCap | 0.2 | None | — | 25 |
| VP/VPro | 0.1 | None | — | 28 |
| VP/SPP | 0.25 | None | — | 139 |
| PEFAm | 0.25 | None | — | 7 |
| PDMAM | 0.5 | None | — | 14 |
| PDEAM | 0.25 | None | — | >1400 |
| PDEAM | 0.05 | None | — | 9 |
| PMAM | 0.5 | None | — | 41 |
| PVP | 0.35 | Na C4 Sulfate | 2.0 | 669 |
| PVP | 0.35 | Na C4 Sulfonate | 2.0 | 493 |
| PEOx | 0.5 | Na C4 Sulfate | 1.0 | 426 |
| PEOx | 0.5 | Na C4 Sulfate | 1.33 | 412 |
| PEOx | 0.5 | Na C4 Sulfate | 1.67 | 516 |
| PEOx | 0.5 | Na C4 Sulfate | 2.0 | >2765 |
| PEOx | 0.5 | NaC8 Sulfonate | 1.0 | 190 |
| PEOx | 0.5 | Na C8 Sulfonate | 3.0 | 287 |
| PEOx | 0.5 | MeOH | 1.0 | >1400 |
| PEOx | 0.5 | MeOH | 3.0 | >1400 |
| PVCap | 0.1 | Na C4 Sulfoante | 1.0 | >1716 |
| VP/VPro | 0.1 | Na C4 Sulfate | 2.0 | 198 |
| VP/SPP | 0.25 | Na C4 Sulfate | 2.0 | 1397 |
| PEFAm | 0.25 | Na C4 Sulfate | 2.0 | 12.2 |
| PEFAm | 0.5 | Na C4 Sulfate | 2.0 | 24 |
| PEFAm | 0.5 | Na C4 Sulfate | 4.0 | >380 |
| PEFAm | 0.5 | MeOH | 1.0 | 26 |
| PEFAm | 0.5 | MeOH | 2.0 | >1300 |
| PDMAM | 0.5 | MeOH | 1.0 | >376 |
| PDMAM | 0.5 | Na C4 Sulfate | 2.0 | >3885 |
| PDEAM | 0.05 | MeOH | 1.0 | >1440 |
| PDEAM | 0.05 | Na C4 Sulfate | 2.0 | >1440 |
| PMAM | 0.5 | MeOH | 1.0 | >1560 |
| PMAM | 0.5 | Na C4 Sulfate | 2.0 | >3885 |

The first row of Table 1 shows results where no additives are present in the THF/SSW control solution. Most of the experiments with polymeric and organic additives used alone demonstrated inhibition effects near or moderately above the threshold inhibition effect at the concentrations indicated. For example, sodium butyl sulfate (Na C4 Sulfate) and sodium butyl sulfonate (Na C4 Sulfonate) each at 2 wt % obtained BSTs of 14.8 minutes and 27.0 minutes, respectively, compared to 7.2 minutes for the control. Therefore, a 2 wt % solution of Na C4 Sulfonate demonstrated an inhibition effect above the threshold inhibition effect with a BST that's 3.75 times the control sample's BST. A 2 wt % solution of Na C4 Sulfate, however, demonstrated an inhibition effect below the threshold inhibition effect with a BST that's only 2.1 times the control sample's BST. Consequently, a higher concentration of Na C4 Sulfate would be required to reach its TIC.

Suprisingly, however, a synergistic inhibition effect occurs when a substantially water soluble polymer is combined with an organic compound having a substantially nonpolar part and substantially polar part and the nonpolar part is an akyl, alkenyl, or alkynyl group 12 or fewer carbon atoms. The synergy for the combination of the first and second additive is evidenced by the combination having a BST or total inhibition effect which is greater than the sum of the respective BST or inhibition effects observed for each additive independent of the other. In one instance, the synergistic inhibition effect was not demonstrated with PEFAm at a concentration below its TIC in combination with Na C4 Sulfate. However, polymeric additives, such as PEFAm or PDMAM, which demonstrated an inhibition effect below the threshold inhibition effect when used alone, did demonstrate a synergistic inhibition effect in combination with an alcohol such as methanol.

In addition to those identified above, applicants believe that the synergistic inhibition effect will be observed with other organic compounds including, but not limited to, nitrogen containing hydrocarbons such as alkyl pyrrolidone, other salts of carboxylic acids, other zwitterions, and other alcohols including ethoxylated alcohols such as 2-butoxy ethanol and diol alcohols such as ethylene glycol or propylene glycol. Also, the substantially nonpolar group may contain one or more double or triple bonded carbon atoms provided the group contains 12 or fewer carbon atoms. Accordingly, the substantially nonpolar group can comprise an alkenyl or alkynl group, as well as, an alkyl group. The presence of a synergistic inhibition effect can be determined by conducting a THF test of a solution containg the first additive, a solution containing the second additive and a solution containing a combination of the first and second additive. A synergism is obtained where the inhibition effect for the combination exceeds the sum of the independent inhibition effects for the first and second additives.

A synergistic inhibition effect can also occur using a polymeric additive which demonstrate good inhibition effects when used alone, such as PDEAM. For example, the synergistic inhibition effect is observed with PDEAM used at a 0.05wt % concentration. Therefore, the synergistic inhibition effect may be observed at very low concentrations for the first additive by conducting a series THF tests with a range of different concentrations for the first additive. Such a series of tests will confirm the presence of the synergistic inhibition effect and demonstrate the extent to which additive concentrations influence such an effect.

As indicated above, the second additives are organic compounds comprising a substantially polar part and substantially nonpolar part with the nonpolar part having an alkyl, alkenyl, or alkynyl group with 12 or fewer carbon atoms. Although not essential to obtaining a synergistic inhibition effect, preferably, the nonpolar part is directly bonded to the polar part. By directly bonded we mean that there are no intervening functional groups between the polar and nonpolar parts which would disrupt the continuity of the bond between the polar and nonpolar part.

The means and method for practicing the invention and the best mode contemplated for practicing the invention have been described. It is to be understood that the foregoing is illustrative only and that other means and techniques can be employed without departing from the true scope of the invention defined in the following claims.

We claim:

1. A method for inhibiting the formation of clathrate hydrates in a fluid having water and other hydrate forming constituents, said method comprising treating said fluid with a first additive and a second additive, said first additive comprising a substantially water soluble polymer and having a first independent effect on the formation of clathrate hydrates in said fluid, said second additive comprising a substantially polar part and a substantially nonpolar part, wherein said nonpolar part is an alkyl, alkenyl, or alkynyl group with 12 or fewer carbon atoms and having a second independent effect on the formation of clathrate hydrates in said fluid, thereby producing a total inhibition effect for said fluid which is greater than the combination of said first and second independent effects for said fluid.

2. The method of claim 1 wherein said second additive has a concentration in said fluid between about 0.05% and about 6% by weight of said water in said fluid.

3. The method of claim 1 wherein said fluid is treated substantially simultaneously with said first and second additive.

4. The method of claim 1 wherein said fluid is treated first with said first additive and treated second with said second additive.

5. The method of claim 1 wherein said fluid is treated first with said second additive and treated second with said first additive.

6. The method of claim 1 wherein said first additive is selected from the group consisting of polyvinyllactams, polyalkylacrylamides, polyalkyloxazolines, polyvinylcarboxylates, and copolymers thereof.

7. The method of claim 1 wherein said second additive is selected from the group consisting of non-ionic, anionic, cationic, zwitterionic organic compounds and mixtures thereof.

8. The method of claim 7 wherein said organic compound is selected from the group consisting of alcohols, ethers, and organic salts.

* * * * *